United States Patent [19]

Larkin

[11] Patent Number: 4,548,606

[45] Date of Patent: Oct. 22, 1985

[54] DUAL COMPARTMENTED CONTAINER WITH ACTIVATING MEANS

[75] Inventor: Mark E. Larkin, Lindenhurst, Ill.

[73] Assignee: Abbott Laboratories, North Chicago, Ill.

[21] Appl. No.: 537,190

[22] Filed: Sep. 29, 1983

[51] Int. Cl.[4] .................... A61M 5/00

[52] U.S. Cl. .................... 604/414; 222/94; 206/222; 604/87

[58] Field of Search .................... 222/80, 81, 85, 86, 222/88, 89, 541, 94; 206/222, 219; 604/408, 410, 411, 414, 416, 82, 85, 86, 87, 88

[56] References Cited

U.S. PATENT DOCUMENTS

| | | | |
|---|---|---|---|
| 3,521,745 | 7/1970 | Schwartzman | 206/222 |
| 4,201,208 | 5/1980 | Cambio, Jr. | 604/411 |
| 4,325,368 | 4/1982 | Kaemmerer | 604/82 |
| 4,396,383 | 8/1983 | Hart | 604/87 |
| 4,411,662 | 10/1983 | Pearson | 604/411 |
| 4,465,488 | 8/1984 | Richmond et al. | 604/414 |

*Primary Examiner*—H. Grant Skaggs
*Assistant Examiner*—Kenneth Noland
*Attorney, Agent, or Firm*—Neil E. Hamilton; Alan R. Thiele

[57] ABSTRACT

A dual compartmented container containing a medicament in one compartment and a diluent in the other with an actuating piercing element operable from outside the container. Mixing of the medicament in one compartment with the diluent in the other is accomplished by moving the piercing element inwardly into the container to pierce a primary diaphragm which seals one of the compartments to outside atmosphere as well as a secondary diaphragm which seals the compartments from each other. The piercing element is constructed and arranged to afford fluid communication between the compartments after it pierces both diaphragms. Intermixing of the contents of the container can thereby be made internally thereof.

13 Claims, 6 Drawing Figures

DUAL COMPARTMENTED CONTAINER WITH ACTIVATING MEANS

BACKGROUND OF THE INVENTION

This invention relates to a dual compartmented container having manual means to intermix the contents of the two compartments from outside the container. More particularly, this invention relates to an additive transfer device which is made a part of a dual compartmented flexible container and will effect communication between the two compartments upon actuation. In this manner the contents of the two compartments can be intermixed within the container and the resulting solution administered intravenously to a patient.

Devices providing separate compartments in a single container for separately enclosing different components in such a way that they may be later intermixed in a single container are described in U.S. Pat. No. 2,176,923 to Nitardy, U.S. Pat. No. 3,290,017 to Davies, et al. and U.S. Pat. No. 3,532,254 to Burke, et al. These devices are deficient in not being able to maintain an effective seal between the two components to be intermixed. Additionally in some instances, a barrier between separate chambers does not adequately withstand the rigors of handling and shipping leading to premature removal. For containers used in health care situations, sterility must be maintained. While many of the prior art devices are simple in configuration the arrangement of parts makes them difficult to sterilize unless the entire device is assembled in a totally sterile environment. Such manufacture is exceedingly expensive.

It is an advantage of the present invention to afford a manually operated dual compartmented container not subject to the aforementioned disadvantages of the prior art such as those relating to sterility and premature activation. Other advantages are: a manually operable dual compartmented container wherein fluid communication between the container compartments is effected by means of a slidable piercing spike; an activating spike for a dual compartmented mixing container which also affords an additive port; a dual compartmented container with an actuating spike which can be fabricated from standard parts utilizing standard sealing techniques. Still other objects and advantages of the present invention will become apparent as the description proceeds.

SUMMARY OF THE INVENTION

The foregoing advantages are accomplished and the shortcomings of the prior art are overcome by the present manually operated dual compartmented container system wherein a container includes wall means and a partition defining two separate compartments for different fluid materials. The partition will include a secondary pierceable diaphragm portion and an end wall will close a portion of the wall means with the end wall being spaced from the partition. Fluid connecting means extend through the end wall and are in fluid communication with the partition. The fluid connecting means include passage means and a primary pierceable diaphragm portion in fluid communication with the container between the end wall and the secondary pierceable diaphragm portion. Activating means are operatively positioned in fluid-tight engagement with the fluid connecting means with the activating means constructed and arranged to pierce both diaphragm portions and provide fluid communication between the compartments through the passage means.

In a preferred manner, the fluid connecting means is provided in part by a tubular member with the first pierceable diaphragm portion positioned therein. The fluid connecting means is further afforded by a tubular portion in fluid-tight engagement with the partition and the secondary pierceable diaphragm portion is positioned as a portion of the partition. The preferred activating means is a slidable piercing pin with a pointed portion dimensioned to extend from a point beyond the secondary diaphragm portion and the primary diaphragm portion in the fluid passage means. The activating means further includes a flexible cover portion secured to the tubular portion and extending over the end of the slidable piercing pin opposite the pointed portions. If desired, a puncturable reseal unit can form a part of the piercing pin opposite the pointed portion for adding additional materials to the container. The fluid connecting means further includes a second member positioned over the first tubular member and extending through the partition and the end wall, with the second tubular member including apertures defining passage means. The second pierceable diaphragm is positioned adjacent the passage means and outwardly thereof. The first and second tubular members include flange portions integrally connected and spaced a distance from the end wall and outwardly thereof to accommodate finger gripping. An additional feature of the invention is a flexible cover portion secured to the flange portions and extending over the end of the slidable piercing pin opposite the pointed portion to act as a flexible cover member.

DESCRIPTION OF THE DRAWINGS

A better understanding of the dual compartmented container with activating means will be had by reference to the drawings wherein.

DESCRIPTION OF THE EMBODIMENTS

Figure 1:
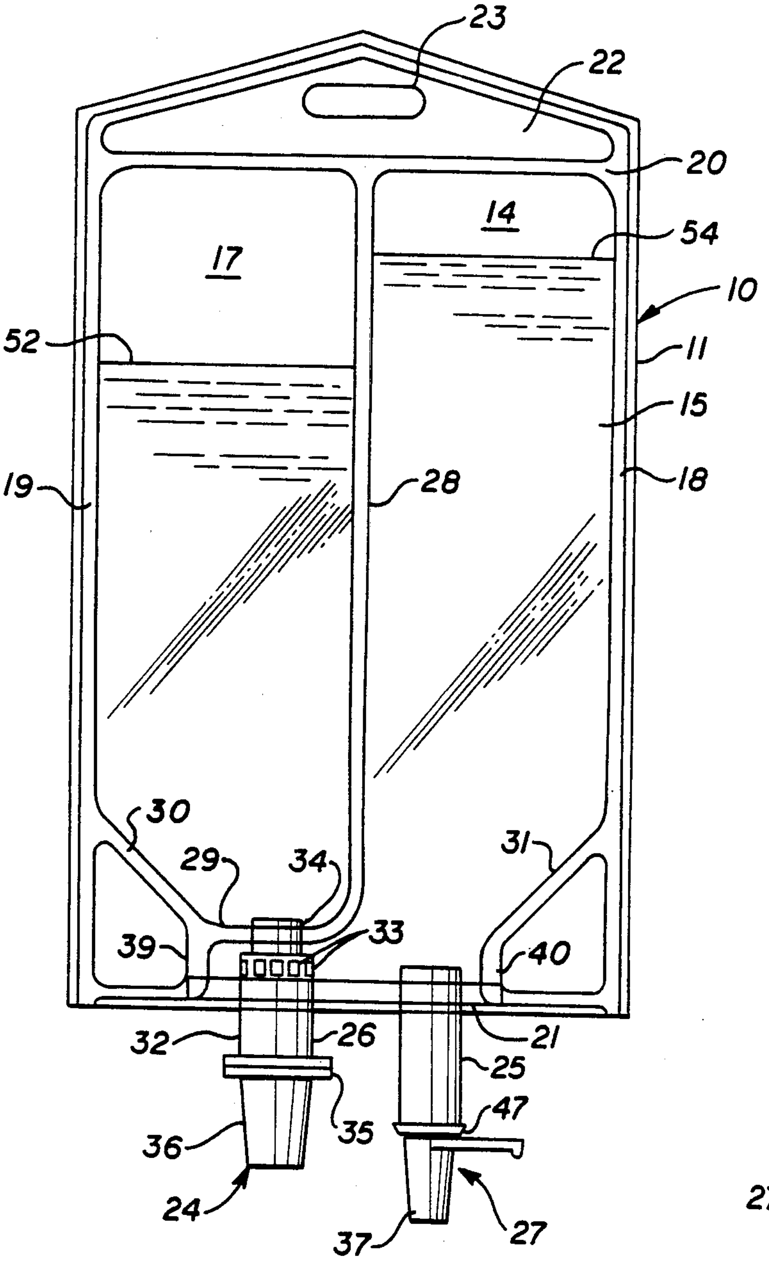
FIG. 1 is a view in front elevation of the dual compartmented container illustrating the two compartments with different components therein.
Figure 2:
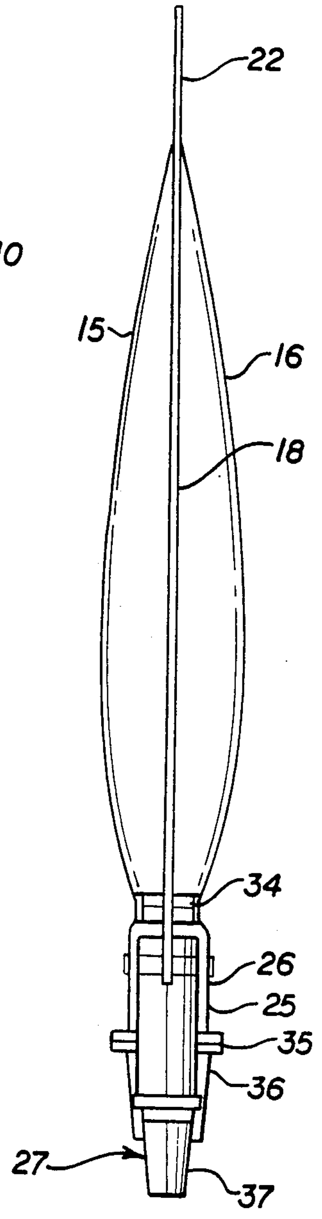
FIG. 2 is a view in side elevation of the dual compartmented container shown in FIG. 1.

Proceeding to a detailed description of the embodiments of the invention, the manually activated dual compartmented container generally 10 is shown in FIGS. 1 and 2. It includes a tubular body section 11 with front and back walls 15 and 16 as well as end walls 20 and 21. Extending from end wall 20 is hanger section 22 with an aperture 23. At the opposite end, two tubular ports 24 and 27 extend through end wall 21. Compartments 17 and 14 are provided in container 10 by means of a longitudinal weld 28 as well as a coextensive transverse weld 29 which is interconnected with an oblique weld 30 and a weld section 39. Additionally, oblique weld 31 and weld section 40 define compartment 14.

Figure 3:
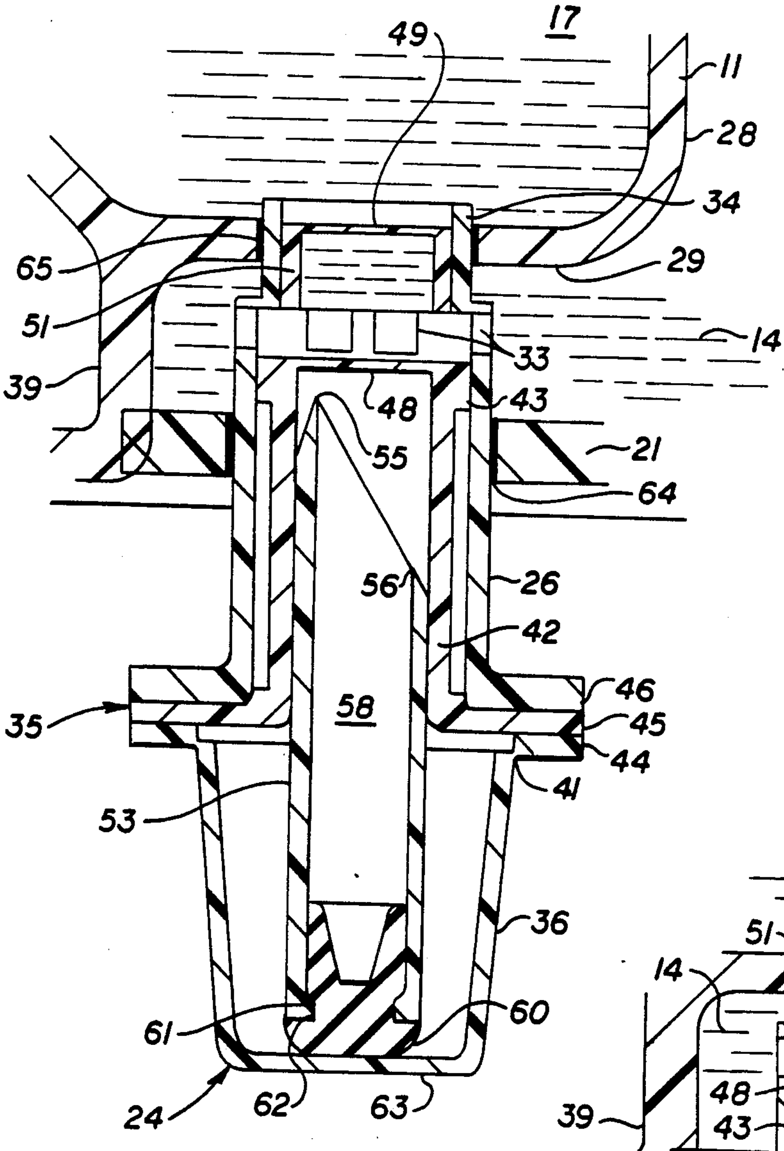
FIG. 3 is an enlarged partial view of the dual compartmented container shown in FIG. 1 illustrating the activating means prior to activation.

As best seen in FIG. 3, tubular port generally 24 is a combined port and activating means as it includes a slidable piercing spike 53 positioned to slide in inner tubular member 42 which includes a flange 45 sealed between flange 44 of flexible cap 36 and flange 46 of outer tubular member 26. Outer tubular member 26 has an extension 34 with apertures 33 in communication with compartment 14. A primary pierceable diaphragm 48 closes the end of inner tubular member 42 and a secondary pierceable diaphragm 49 extends over the end of inner portion 51 which is secured to extension 34. Piercing spike 53 has an oblique end section terminating in an outer point 55 and an inner point 56. Spike 53 has at the opposing end a reseal plug 60 held by spike 53 through undercut 61 on plug 60 and flange 62 on spike 53.

FABRICATION

The dual compartmented container will be formed from two opposing sheets of plastic material such as polyvinylchloride. These will be sealed along seal lines 18, 19, 20 and 21 (except for the portion where the tubular ports 24 and 27 are to be placed. In this instance, ports 24 and 27 will be mandrel sealed such as at 64 and 65, see FIG. 3). It will be appreciated that port 24 will be preassembled with spike 53 placed therein. It will be further appreciated that only outer tubular member 26 will be mandrel sealed through end wall 21 as well as transverse weld 29. This is to allow the partial filling of compartment 17 with a powdered or liquid material which can be a penicillin product, a vitamin or a nutritional preparation indicated by numeral 52. After filling to the desired degree, inner portion 51 with diaphragm 49 will be sealed in the extension 34 of tubular member 26 such as by RF welding or heat sealing. Compartment 14 will be partially filled with a diluent such as water or dextrose indicated by numeral 54. After the desired filling of the two compartments 17 and 14, inner tubular member 42 with diaphragm 48 will be sealed to flange 46 and cover cap 36 will also be sealed to flange 45. Simultaneously with the sealing of tubular port 24 to container body 11, tubular port 27 will likewise be sealed to container body 11. This is accomplished by mandrel sealing outer tubular member 25 to and through end wall 21. It will be appreciated that tubular port 27 also includes a smaller diameter tubular member 38 (see FIG. 6) which is solvent sealed to tubular member 25 along its contacting surfaces inside flange 47 with flange 47 affording an abutment surface for tubular member 25. The usual diaphragm will be positioned in tubular member 25 adjacent flange 47. A protective cap 37 will be placed over inner tubular member 38. The contents of the container are then ready to be sterilized.

Prior to activation, dual compartmented container 10 will be substantially in the form indicated in FIG. 1. The only difference is that it will be included in an overwrap after sterilization, if a sterile procedure is not employed, which can be effected by heat or radiation. Also, it should be pointed out that in the event that the component in compartment 17 indicated by numeral 52 is a powder, this portion of the bag represented by compartment 17 will be covered with a foil such as aluminum/-polyester polypropylene which can be secured by RF or heat welding.

In certain instances where a sterile filling procedure is not employed, the materials placed in compartments 14 and 17 may require different sterilization conditions. This may necessitate a two-stage sterilization procedure. When this occurs the least sensitive material can be placed in compartment 14 and a removable plug (not shown) positioned in tubular port member 26 and in place of inner tubular member 42 and inner portion 51 with diaphragm 49. After sterilization, the plug would be removed, the more sensitive material placed in compartment 17 and inner tubular member 42 sealed in tubular member 26 with member 42 sealed to flange 46 as previously indicated. Alternatively, in the event component 52 is heat sensitive, compartment 14 could be filled and sealed as previously indicated, after diluent 54 is placed therein and thermally sterilized. With inner tubular port member 42 and inner portion 51 sealed in place, a fill tube in communication with compartment 17 can be positioned through end wall 21 and weld 30. The fill tube will be pinch-sealed but cut open after sterilization for filling with component 52 and resealed by heat pinching.

OPERATION

Figure 4:
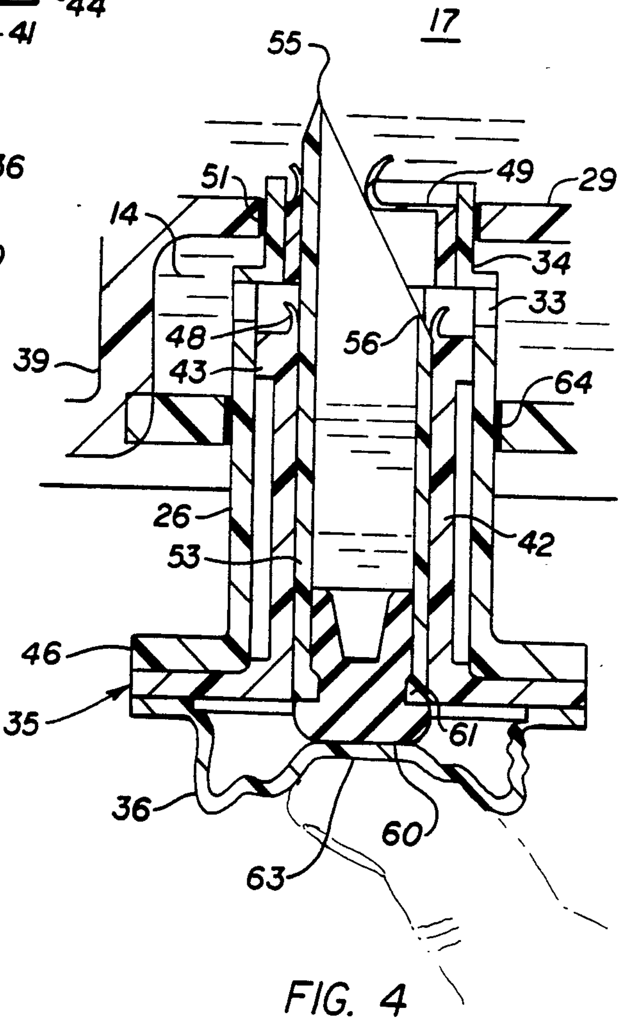
FIG. 4 is a view similar to FIG. 3 showing the activating means in an activated position with fluid communication between the two compartments of the container.
Figure 5:
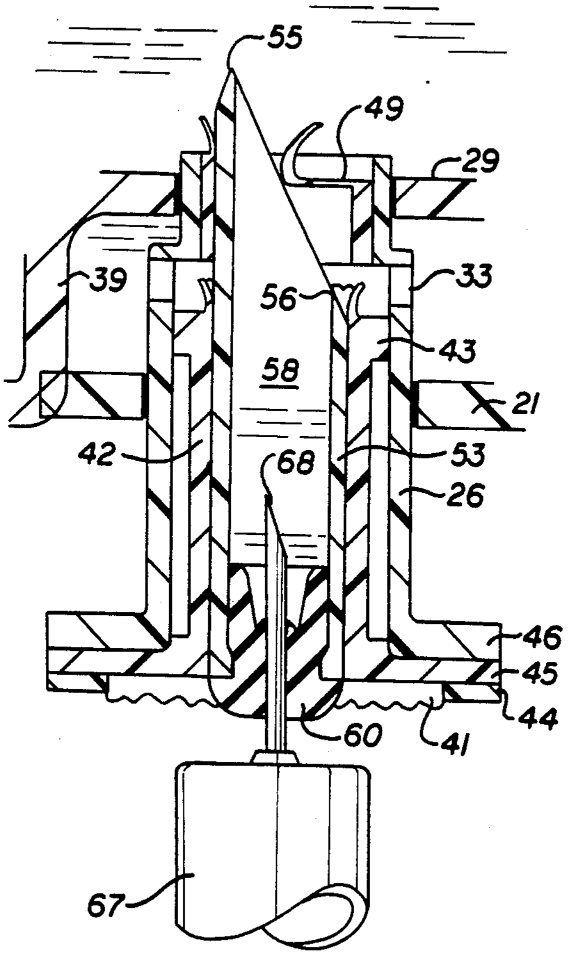
FIG. 5 is a view similar to FIG. 4 illustrating the method of introduction of an additive material to the container through the activating piercing pin.

A better understanding of the advantages of dual compartmented container with its associated activating means will be had by a description of its operation. At the time of usage, all that is required to intermix the component 52 in compartment 17 with the component 54 in compartment 14 is to place one's fingers over the inside of flanges generally 35 and the thumb on the outside top of cap 36. This is illustrated in FIG. 4. A force will be applied with the thumb to slide piercing spike 53 inwardly in tubular member 42 to pierce through diaphragm 48 as well as diaphragm 49. When the spike reaches a position as illustrated in FIG. 4, it will be seen that a fluid pathway will be created between compartment 17 and compartment 14. This is effected in part by means of apertures 33 in tubular member 26 and the fluid channel 58 in spike 53 with the outer point 55 and the inner point 56 of the spike being positioned to effect such interflow. This is afforded be extending the end or point 55 of spike 53 from beyond diaphragm 49 with end or point 56 beyond diaphragm 48.

Figure 6:
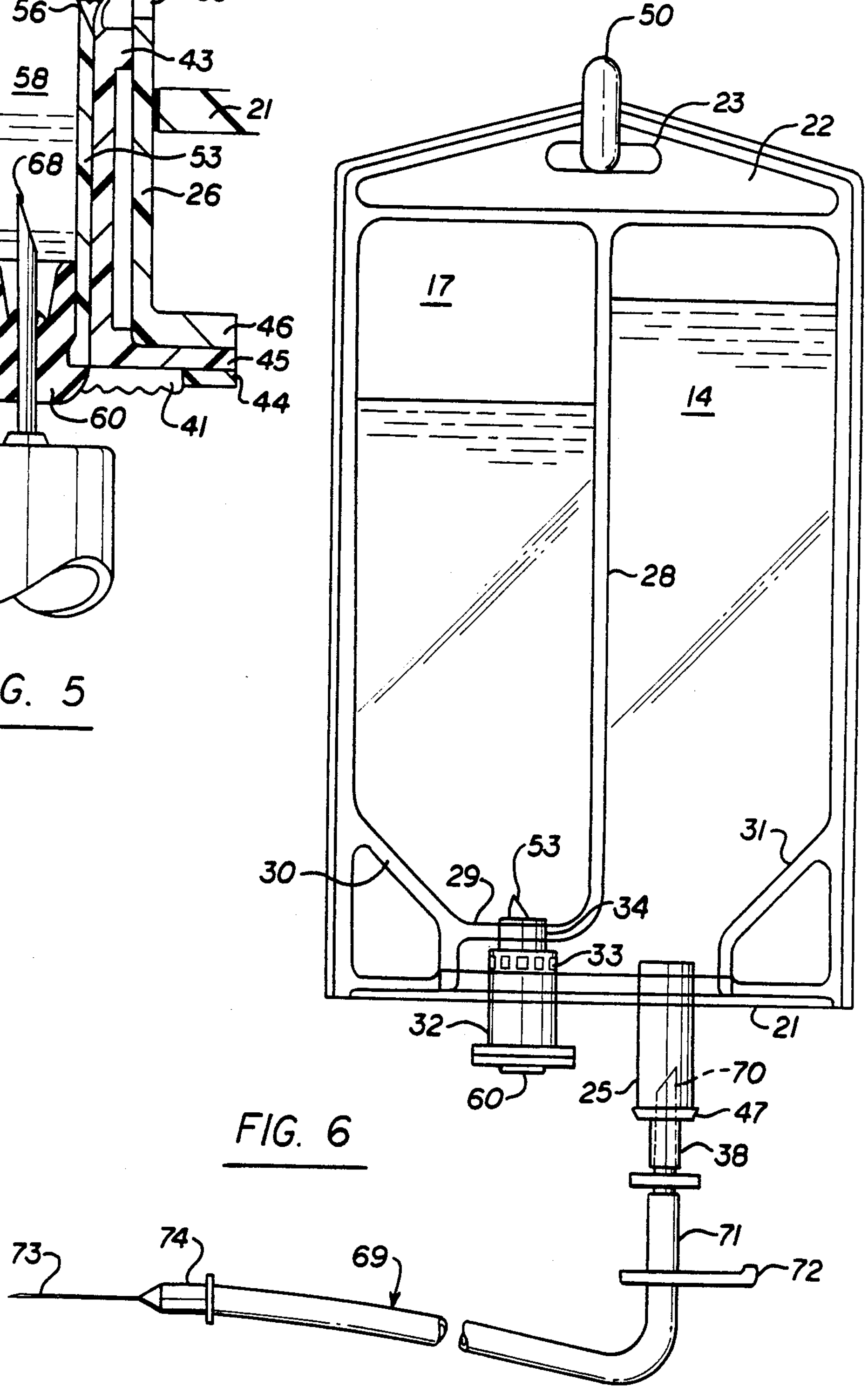
FIG. 6 is a view in side elevation depicting the container after it has been activated and an intravenous administration set placed in fluid communication therewith.

If it is desired to add a therapeutic drug such as insulin, vitamins, etc. into the mixed solution, cover cap 36 is so designed that it can be easily removed from flange 44 with a frangible section being indicated at 41. This addition is made by means of syringe 67 with hypodermic needle 68 which is easily inserted through reseal plug 60. After this suitable addition, a typical administration set generally 69 will be placed in fluid communication with tubular port 25 after removal of cover cap 37. This is illustrated in FIG. 6 with the typical administration set including a piercing spike 70 interconnected with tubing 71 upon which is placed a clamp 72. Tubing is interconnected with a needle adapter 74 which makes the connection with hypodermic needle 73.

While the present dual compartmented container 10 has been preferably described for use with a powdered medicament in compartment 17 and a liquid in compartment 14, it is obvious that the container is usable with any fluid material. For example, a liquid could be placed in compartment 17 as well as in compartment 14. Further, while the present container system has been described for use with fluid materials in the health care field, it will be appreciated that the dual compartmented container system can be applied to other fields. For example, it would have application with any fluid materials where it is necessary to maintain two materials in separate condition until prior to mixing and use, and where one of the materials is sensitive to ambient conditions of the other material. It should further be understood that the term "fluid material" as employed in the specification or claims is meant to imply any medicament or diluent material which will flow from one compartment to another, whether a liquid, solid or gas.

The preferred material for manufacturing a body section 11 with front and back walls 15 and 16 is a polyvinylchloride resinous plastic material. However, other resinous plastics such as polypropylene or polyester could be used. The preferred materials for composing the tubular ports 24 and 27 are polyvinylchloride. However, other semirigid plastic materials such as polypropylene or polyester could also be utilized. The reseal plug 60 is of the standard butyl rubber variety. However, rubber-like plastics such as styrene-butadiene polymers could be substituted.

It will thus be seen that through the present invention there is now provided a manually operable dual compartmented container which is easily utilized and manufactured. The container system of this invention affords a sterile environment for the fluid materials of any type during storage as well as mixing. Activation of the system is readily accomplished without the use of additional components with the activation system also serving as a means of adding additional components to the system.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

What is claimed is:

1. A container system for separately storing and subsequently mixing the fluid contents of at least two compartments in the container comprising:

a container including wall means and a partition defining two separate compartments for different fluid materials, said partition including a secondary pierceable diaphragm portion;

an end wall closing a portion of said wall means, said end wall spaced from said partition;

fluid connecting means extending through said end wall and in fluid communication with said partition, said fluid connecting means further comprising:

a first tubular member having a primary pierceable diaphragm therein, said tubular member being in fluid-tight engagement with said partition and said secondary pierceable diaphragm;

a second tubular member positioned over said first tubular member, said second tubular member extending through said partition in said end wall, said first and second tubular members including apertures defining said passage means;

activating means operatively positioned in fluid-tight engagement with said fluid connecting means, said activating means constructed and arranged to pierce both said diaphragm portions and provide fluid communication between said compartments through said passage means.

2. The container system as defined in claim 1 wherein said activating means is defined by a slidable piercing pin with a pointed portion dimensioned to extend from a point beyond said primary diaphragm portion to said fluid passage means.

3. The container system as defined in claim 2 wherein said activating means further includes a flexible cover portion secured to said tubular portion defining said fluid connecting means and extending over the end of said slidable piercing pin opposite said pointed portion.

4. The container system as defined in claim 3 further including a cannula puncturable reseal component positioned in said piercing pin opposite said pointed portion.

5. The container system as defined in claim 1 wherein said secondary pierceable diaphragm is positioned adjacent said passage means and outwardly thereof.

6. The container system as defined in claim 1 wherein said first and second tubular members include flange portions integrally connected and spaced a distance from said end wall to accommodate finger gripping.

7. The container system as defined in claim 6 wherein said activating means further includes a flexible cover portion secured to said flange portions of said first and second tubular members and extending over the end of said slidable piercing pin opposite said pointed portion.

8. An activator device for intermixing the separated contents of a partition container having an internal portion dividing said container into first and second compartments and also having an end wall comprising:

a tubular member positioned in fluid-tight engagement with said partition and extending through said end wall in a fluid-tight manner;

fluid passage means extending through said tubular member and positioned between said partition and said end wall and in communication with said second compartment, said fluid passage means further including a second tubular member positioned over said fluid-tight tubular member, said second tubular member adapted to extend through said partition and said end wall, said first and second tubular members including apertures defining in part said fluid passage means;

first and second pierceable diaphragms positioned in said tubular member, said first diaphragm placed between said fluid passage means and the first compartment; and activating means operatively positioned in fluid-tight engagement with said first tubular member, said activating means constructed and arranged to pierce both said diaphragm portions and provide fluid communication between said compartments through said passage means.

9. The activator device as defined in claim 8 wherein said activating means is defined by a slidable piercing pin with a pointed portion dimensioned to extend from a point beyond said second diaphragm portion to said fluid passage means.

10. The activator device as defined in claim 8 wherein said activating means further includes a flexible cover portion secured to said tubular member at the end of said slidable piercing pin opposite said pointed portion.

11. The activator device as defined in claim 10 further including a cannula puncturable reseal component positioned in said piercing pin opposite said pointed portion.

12. The activator device as defined in claim 8 wherein said first and second tubular members include flange portions integrally connected and spaced a distance from said end wall to accommodate finger gripping.

13. The activator device as defined in claim 12 wherein said activating means further includes a flexible cover portion secured to said flange portions of said first and second tubular members and extending over the end of said slidable piercing pin opposite said pointed portion.

* * * * *